(12) United States Patent
Amor et al.

(10) Patent No.: US 6,183,494 B1
(45) Date of Patent: Feb. 6, 2001

(54) MICROCOMMISSUROTOMY DEVICE WITH LEVERS

(75) Inventors: Georges Amor, Saint-Max; Brice Letac, Mont-Saint-Aignan; Alain Cribier, Maronne; Thierry Rimlinger, Laitre-sous-Amance, all of (FR)

(73) Assignee: Medicorp S.A., Villers-les-Nancy (FR)

( * ) Notice: Under 35 U.S.C. 154(b), the term of this patent shall be extended for 0 days.

(21) Appl. No.: 09/077,464

(22) PCT Filed: Jan. 6, 1997

(86) PCT No.: PCT/FR97/00013

§ 371 Date: Nov. 16, 1998

§ 102(e) Date: Nov. 16, 1998

(87) PCT Pub. No.: WO97/25092

PCT Pub. Date: Jul. 17, 1997

(30) Foreign Application Priority Data

Jan. 5, 1996 (FR) .................................................. 96 00064

(51) Int. Cl.⁷ .................................................. A61M 29/00
(52) U.S. Cl. .............................................................. 606/198
(58) Field of Search ..................................... 606/198, 194, 606/108; 604/53, 105, 108; 600/210

(56) References Cited

U.S. PATENT DOCUMENTS

| 832,201 | * | 10/1906 | Kistler ................................. 606/198 |
| 1,331,737 | * | 2/1920 | Ylisto ................................... 606/198 |
| 4,585,000 | | 4/1986 | Hershenson . |
| 5,279,565 | * | 1/1994 | Klein et al. ............................ 604/105 |

FOREIGN PATENT DOCUMENTS

| 0401158 | 12/1990 | (EP) . |
| 2071338 | 9/1990 | (FR) . |
| 146026 | 7/1920 | (GB) . |
| 509276 | 5/1976 | (SU) . |
| 9521593 | 8/1995 | (WO) . |

* cited by examiner

Primary Examiner—Michael H. Thaler
Assistant Examiner—Tan-Uyen T. Ho
(74) Attorney, Agent, or Firm—Roylance, Abrams, Berdo & Goodman, L.L.P.

(57) ABSTRACT

A retractor is mounted at the distal end of a catheter. The retractor is constituted of two symmetrically deformable parallelograms. In the closed position, the retractor has substantially the same radial extension as the catheter.

14 Claims, 1 Drawing Sheet

MICROCOMMISSUROTOMY DEVICE WITH LEVERS

Figure 1:
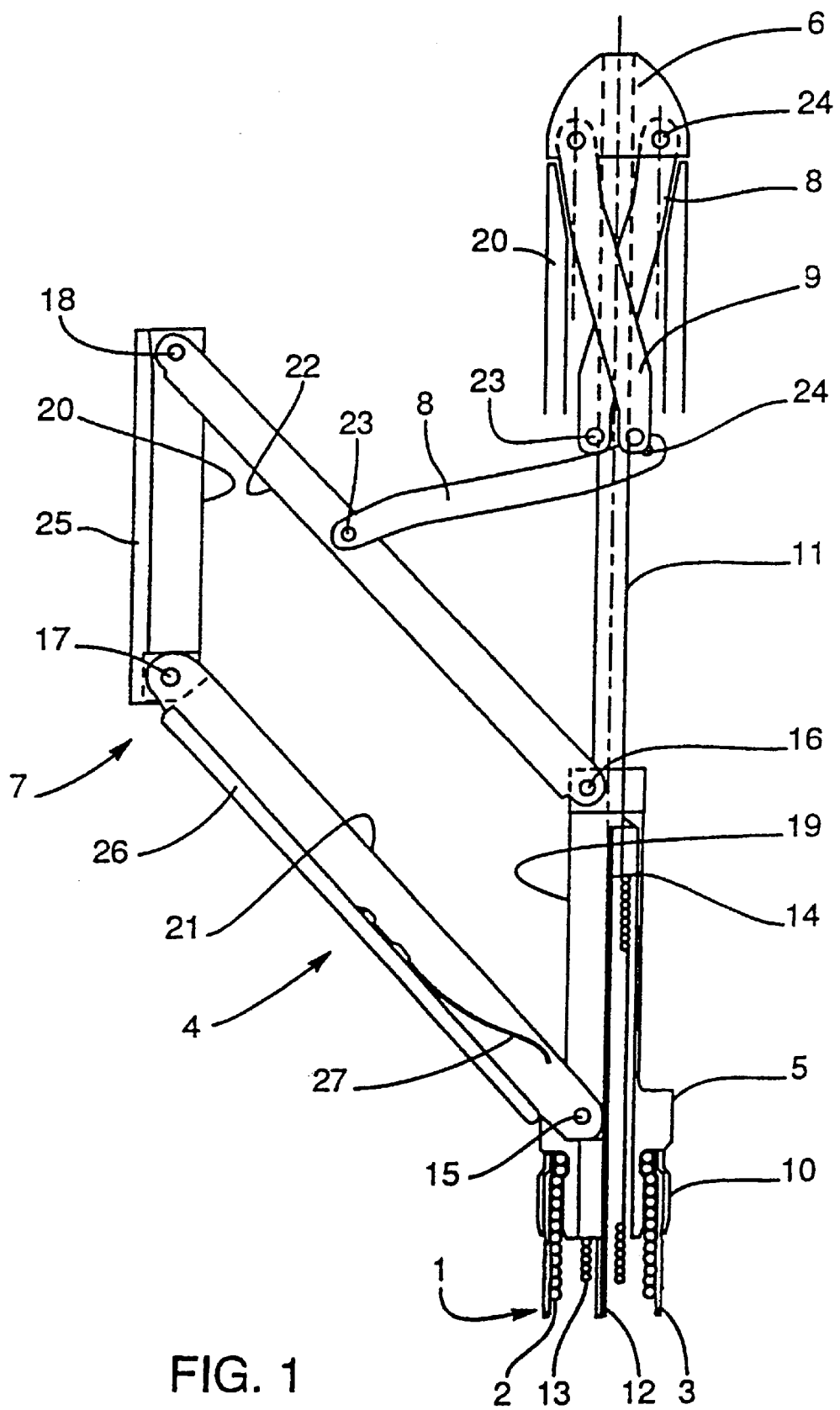

The invention concerns a microcommissurotomy device with levers, in other words an apparatus serving as a cardiac catheter intended to eliminate the stenosis of cardiac valvulae by separation of the valvular commissures by means of a levered retractor under manual control.

FR-A-2.071.338 describes an apparatus of this type comprising a resilient base traversed by an axial shaft for the maneuvering. At the proximal end of the resilient base is arranged a handle for manual control. At the distal end, the resilient base is integral with a tubular casing or a socket in which can slide a slide member affixed to the end of the axial shaft. A retractor constituted of two parallel arms is arranged around the socket-slide assembly. Each of the two arms is retained at its proximal end by a helical spring attached to a ring integral with the resilient base. This spring is intended to prevent the arm from catching on the cardiac tissue. At its distal end, each arm is articulated on the end of a lever of which the other end is articulated on the socket member integral with the resilient base. This lever is articulated at its midpoint on a second lever of which one end is articulated on the slide attached to the end of the axial shaft, and of which the other end slides without obstruction in the arm of the side of its proximal part.

This apparatus is arranged for engagement in the heart by the finger of the surgeon, then it is set in action by the manual control which assures a relative movement of the axial shaft and the resilient base, in other words including the slide and the socket. In the course of this movement, the points of articulation of the two levers of each arm situated respectively on the slide and the socket come closer together. The result is a distancing of their mutual point of articulation and a distancing of the arm in relation to the axial shaft and the resilient base. The distancing movement is symmetrical and the two arms are separated from another while remaining parallel to one another. This movement suffices to eliminate the stenosis of the cardiac valvulae.

This apparatus is intended to be inserted into the heart through the wall of one auricle, by means of the finger of the surgeon, and that is why it is limited to use in cases of invasive procedures.

Besides, when this apparatus is closed, the three points of articulation of the levers of one arm, in other words the point of articulation of the first lever on the socket, the point of articulation of the second lever on the slide, and the point of mutual articulation of the two levers on one another, essentially at their midpoint, are in alignment for all practical purposes. The result is that the opening of the arms of the retractor is generally sudden or abrupt, which can negatively influence the precision required for this type of intervention.

One object of the present invention is to propose a microcommissurotomy device not requiring invasive intervention.

Another object of the invention is to provide an arrangement of levers which avoids any shock or sudden stoppage upon opening of the retractor.

Still another object of the invention is to propose an accessory arrangement for opening the retractor.

Finally, another object of the invention is to propose an apparatus which can be located and pin-pointed precisely by imagery techniques.

The object of the present invention is a microcommissurotomy device with levers, comprising a retractor with two active sides being displaced symmetrically and essentially parallel to the axis of the retractor, the opening of the retractor being assured by manual control by movement of the distal end of the retractor in relation to its proximal end socket, characterized in that the retractor is mounted at the distal end of a catheter, and characterized in that, in closed position, the retractor has a radial bulk or extension essentially equal to that of the catheter.

According to other characteristics of the invention:
- the retractor is constituted of two symmetrically deformable parallelograms which are symmetrically deformable in relation to the axis of the retractor, of which the first side is constituted by the proximal end socket of the retractor and the second side by the active side;
- the third side of the parallelogram is articulated on the socket and carries a plate spring which, when the retractor is in closed setting, pulls said third side toward the exterior;
- the fourth side of the parallelogram, in the vicinity of its midpoint, presents an articulation point for a small rod which is articulated at its other end on the distal end of the retractor;
- the two articulation points of the small rod are situated on one and the other side of the axis of the retractor;
- the small rods of each of the two symmetrical parallelograms of the retractor are intersecting;
- the distal end of the retractor is carried by a tube sliding in the proximal socket of the retractor;
- the tube is connected to a traction wire and slides in a flexible internal member within the catheter, the forces of traction and compression being transmitted from the proximal end to the distal end of the catheter by virtue of the combination of the traction wire and the flexible internal member within the catheter;
- the tube opens at the distal end of the retractor to constitute a passage to a guide in the form of metal wire for the guiding of the retractor as far as the site of the commissurotomy;
- the guide in the form of metal wire carries a flexible end, which is atraumatic and, to the right of the connection between the guide and its flexible end, a separate olivary member with the capacity to cooperate with the distal end of the retractor to secure complete opening of the retractor;
- the catheter secures the longitudinal positional maintenance of the retractor at the site of the commissurotomy;
- when the retractor is in open position, its distal end is located between the two active sides of the retractor;
- the active sides of the retractor are covered with a slide prevention covering;
- the retractor is constituted of one or more materials which are capable of assuring that it can be precisely located by imagery techniques using X-rays or ultrasound;
- the retractor and the catheter are covered with a biologically compatible covering.

Other characteristics of the invention are disclosed in the following description with reference to the attached drawing of which the single FIGURE diagrammatically and partially represents the distal end of one exemplary embodiment of a microcommissurotomy device with one part in open position, the other part in closed position.

According to the invention, the microcommissurotomy device with levers includes at its distal end a retractor having small diameter, mounted on a catheter to be introduced through a blood vessel, for example an artery, and having a manual control at its proximal end.

The catheter 1 is constituted of a flexible metal external member 2, in the form of a helical spring, and a flexible plastic exterior sheathing 3, covering the flexible external member 2. At the distal end of catheter 1 is mounted the retractor 4, constituted essentially of a proximal end socket 5, a distal end 6, two deformable parallelograms 7 (of which only one is shown), and two intersecting small rods 8 and 9.

Proximal end socket 5 is affixed rigidly to the distal end of catheter 1, for example by means of an inset ring 10. It presents a certain length and is traversed axially by a tube 11 abutting at the distal end 6 of retractor 4 and opening beyond the end of distal end 6. In the example shown, tube 11 is attached to metal wires 12 of uniform length, which can be rectilinear or in intersecting helices, and which are traction wires connected to the manual control arrangement, not shown, at the proximal end of the microcommissurotomy device. A flexible member 13 is provided surrounding wires 12, in the form of a helical spring inside catheter 1, of which the end 14 is lodged in socket 5.

Two deformable parallelograms 7, of which only one is shown in the drawing, are arranged symmetrically to the axis of socket 5 and tube 11. One parallelogram 7 is defined by its four corners 15, 16, 17, 18, which constitute the reciprocal articulation points for the sides of the parallelogram.

The first side 19, between articulation points 15 and 16, is constituted for all practical purposes by a length of socket 5. The second side 20, parallel to first side 19, is the active side of the microcommissurotomy device. It is this side which secures performance of the commissurotomy by being displaced parallel to the axis of the retractor. The third side 21 is located between articulation points 15 and 17. The fourth side 22, parallel to third side 21, constitutes the opening lever of retractor 4. In the vicinity of its midpoint, fourth side 22 carries an articulation point 23 for small rod 8 of which the other end is articulated on the distal end 6 at articulation point 24.

When retractor 4 is in closed setting, small rod 8 is in the position shown at the top of the drawing. Side 22 is then applied longitudinally against tube 11 and side 20 is in the position shown at the top of the drawing. Sides 20 and 21 are then arranged with one as the extension of the other. They present a semi-cylindrical mounting, respectively numbered 25 and 26, to the exterior at the end. As retractor 4 is symmetrical, it is completely contained in the interior of the exterior cylindrical surface of mounting arrangement 25, 26 and of the symmetrical mounting of the other parallelogram 7. The circular section of this cylindrical surface corresponds to the dimensions of socket 5 and the ogival head of distal end 6. The radial bulk or extension of retractor 4 in closed position is thus essentially the same as that of catheter 1 and its insertion as far as the heart can be assured by catheterization by passing through a blood vessel and particularly through an artery.

Small rods 8 and 9 are intersecting. Small rod 8, for example, has its one articulation point 24 on distal end 6 of one side of tube 11 and its other articulation point 23 on fourth side 22, on the other side of tube 11. Thus, tube 11 which is subjected to traction by wire 12 is between the two articulation points 23 and 24 which facilitates the opening of retractor 4.

Within mounting 26, third side 21 of parallelogram 7 carries a plate spring 27. When retractor 4 is in closed position, the spring engages on socket 5 and pulls the third side 21 toward the exterior.

The operation of the microcommissurotomy device according to the invention is controlled in the following manner. Preferably, a guide is arranged starting from a blood vessel, for example an artery, passing at least as far as the valvula presenting a stenosis. This guide is for example in the form of a metal wire.

Advantageously, this rigid guide is terminated by a flexible end, which is atraumatic, of several centimeters for example 10 cm in calibration, and intended to facilitate the arrangement of the guide. Preferably, to the right of the connection between the rigid guide and its flexible end is provided a separate olivary member, capable of playing a role at the moment of the commissurotomy procedure.

When the microcommissurotomy device is at rest, wire 12 is pulled toward distal end 6 and flexible member 13 is pulled toward the proximal end of the catheter in such a manner that retractor 4 is maintained in closed position (top part of the drawing). The proximal end of the guide is introduced into tube 11 by distal end 6 of retractor 4. The assembly of retractor 4 and catheter 1 is then introduced into the blood vessel being guided by the guide until it reaches the valvula having a stenosis.

It is advantageous that retractor 4 is constituted of one or more materials allowing its precise location to be pinpointed by imagery techniques, for example by X-ray or ultrasound.

When retractor 4 is in the desired position, it is held by the guide which limits its lateral movements caused by variations of the blood flow. The external flexible member 2 of catheter 1, covered by plastic sheath 3, works by compression to secure the maintenance of retractor 4 in longitudinal position on the guide. The opening of retractor 4 is then triggered by manual control, by pressure on flexible internal member 13 and traction on wire 12, the thrust on flexible member 13 intervening so that the single flexible member 2 of the catheter need not equalize the traction of wire 12 without support.

The traction force is transmitted from wire 12 to tube 11 and to distal end 6 of the retractor. This axial force is applied between the two articulation points 23 and 24 of small rod 8, (and between the two corresponding articulation points of small rod 9, the two small rods 8 and 9 being in intersecting arrangement), which avoids a sudden stoppage of operation upon opening. The plate spring 27 begins to move the third side 21 of parallelogram 7 away from socket 5 (a symmetrical movement for opening is applied to the other parallelogram of retractor 4). In this opening movement, the fourth side 22 is opened parallel to third side 21 and second side 20 is moved away from the axis of the retractor while remaining parallel thereto. Due to the fact that the articulation point 23 on fourth side 22 moves away from the axis of the retractor, small rod 8 pivots and has a tendency to take an inclined position relative to the axis of the retractor, which facilitates the withdrawal movement of tube 11 and distal end 6. Fourth side 22 plays the role of lever to assure the opening of retractor 4 until it reaches completely open position as shown at the bottom of the drawing, small rod 8 then having its articulation point 24 in the position represented in the drawing, and distal end 6 being covered in the space defined by the two halves of retractor 4.

In the course of this opening of retractor 4, it is the second sides 20 of the deformable parallelograms 7 which secure the commissurotomy.

With this in mind, the exterior surface of their mounting 25 is advantageously covered by a slide prevention covering.

It can occur that the stenosis is of such magnitude or dimensions that the opening of retractor 4 is not complete.

It is possible to use the guide for the catheter to give more opening power to the retractor so as to completely separate the commissures of the valvula. Traction on the guide then allows force to be applied on distal end 6 by means of the separate olivary member at the end of the rigid guide. Thus, the cooperation of the separate olivary member and distal end 6 allows for securing complete opening of the retractor and a satisfactory commissurotomy.

The microcommissurotomy device can advantageously be provided with a device allowing for measurement of the blood pressure to the right of the retractor. This measuring device can be for example a channel arranged in the sheathing of the catheter and filled with liquid, the channel opening in the central part of the retractor and being in connection, in the proximal part of the catheter, with a pressure detector. Moreover, this channel can be used for injection of a product providing contrast or also a treatment liquid.

Besides, it is preferable to provide the pieces being subjected to friction with an antiwear covering to avoid the appearance of play affecting the precision of the surgical operation. Finally, it is desirable to cover all of the elements of the

What is claimed is:

1. A microcommissurotomy device with levers (4) comprising:

a proximal end socket (5) affixed rigidly to the distal end of a catheter (1), a member (11) axially traversing the proximal end socket and terminating at the distal end (6) of a retractor, and two articulated parallelograms (7) arranged symmetrically in relation to the member (11) of the retractor, each parallelogram being constituted of one active arm (20) parallel to the axis of the retractor and two parallel levers (21, 22) articulated at one end (17, 18) on said arm, the opening of the retractor being secured by manual control by movement of the distal end (6) of the retractor in relation to its proximal end socket (5) to displace the active arms (20) parallel to the axis of the retractor, the retractor in closed position having a radial bulk or extension essentially equal to that of the catheter (1), wherein the levers (21, 22) are articulated at their opposite end (15, 16) on the proximal end socket (5) and in that each parallelogram (7) is connected to the distal end (6) of the retractor by a small articulated rod (8, 9).

2. The microcommissurotomy device as in claim 1, wherein the distal lever (22) of each parallelogram (7) in the vicinity of its midpoint presents an articulation point (23) for the small rod (8, 9) articulated at its other end (24) on the distal end (6) of the retractor (4).

3. The microcommissurotomy device as in claim 2, characterized in that the two points of articulation (23, 24) of the small rod (8, 9) are situated one on either side of the member (11) of the retractor (4).

4. The microcommissurotomy device as in claim 3, characterized in that the small rods (8, 9) of the two symmetrical parallelograms (7) of the retractor (4) are intersecting.

5. The microcommissurotomy device as in one of the preceding claims, wherein the proximal lever (21) of each parallelogram (7) carries a plate spring (27) which, when the retractor (4) is in closed position, pulls said proximal lever (21) toward the exterior.

6. The microcommissurotomy device as in one of the preceding claims, wherein the distal end (6) of the retractor (4) is in the form of an ogival head carried by a tube (11) sliding in the proximal end socket (5) of the retractor.

7. The microcommissurotomy device as in claim 6, wherein in the tube (11) opens at the distal end (6) of the retractor (4) to constitute a passage for a guide in the form of a metal wire for the guiding of the retractor until it reaches the site of the commissurotomy.

8. The microcommissurotomy device as in claim 7, wherein in the guide in the form of metal wire carries a pliable end, which is atraumatic, and, to the right of the connection between the guide and its pliable end, a separate olivary member with the capacity to cooperate with the distal end (6) of the retractor to secure complete opening of the retractor.

9. The microcommissurotomy device as in one of the preceding claims, characterized in that the member (11) of the retractor is connected to at least one traction wire (12) and slides in a flexible member (13) within the catheter (1), the forces of traction and compression being transmitted from the proximal end to the distal end of the catheter by virtue of the combination of the traction wire (12) and the flexible member (13) within the catheter (1).

10. The microcommissurotomy device as in one of the preceding claims, characterized in when the retractor (4) is in open position, its distal end (6) is located between the active arms (20) of the retractor (4).

11. The device as in one of the preceding claims, characterized in the active arm (20) and the proximal lever (21) of each parallelogram (7) present a semi-cylindrical mounting (25, 26) on the exterior, so that the retractor (4) is contained entirely within the cylindrical exterior surface formed by the symmetrical mountings of the two parallelograms (7) in closed position.

12. A catheter (1) intended to be mounted between the distal retractor (4) and the proximal manual control of the microcommissurotomy device as in one of the preceding claims, wherein the catheter comprises:

a flexible external member (2) and a pliable exterior sheathing (3) covering the flexible external member, at least one internal traction wire (12) intended to be connected by the one end to said proximal manual control and by the other end to the sliding distal end (6) of the retractor (4), a flexible member (13), within the catheter (1), in which flexible member (13) slides the traction wire (12), the forces of traction and compression being transmitted from the proximal end to the distal end of the catheter by virtue of the combination of the traction wire (12) and the internal flexible member (13).

13. A catheter as in claim 12, wherein in that the flexible members (2, 13) are in the form of helical springs.

14. A catheter as in claim 12 or 13, wherein the catheter in that it comprises a plurality of traction wires (12) of uniform length in rectilinear or intersecting helices.

\* \* \* \* \*